US009642636B2

(12) United States Patent
Ariura et al.

(10) Patent No.: US 9,642,636 B2
(45) Date of Patent: May 9, 2017

(54) EXPANSION INSTRUMENT

(71) Applicant: TERUMO KABUSHIKI KAISHA, Shibuya-ku (JP)

(72) Inventors: Shigeki Ariura, Ebina (JP); Masakatsu Kawaura, Sunnyvale, CA (US)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 322 days.

(21) Appl. No.: 14/283,834

(22) Filed: May 21, 2014

(65) Prior Publication Data
US 2014/0350330 A1 Nov. 27, 2014

Related U.S. Application Data

(63) Continuation of application No. PCT/JP2012/069684, filed on Aug. 2, 2012.

(30) Foreign Application Priority Data

Nov. 22, 2011 (JP) ................................ 2011-255412

(51) Int. Cl.
*A61M 29/00* (2006.01)
*A61B 17/22* (2006.01)
(Continued)

(52) U.S. Cl.
CPC .... *A61B 17/22032* (2013.01); *A61B 17/0206* (2013.01); *A61B 17/0218* (2013.01);
(Continued)

(58) Field of Classification Search
None
See application file for complete search history.

(56) References Cited

U.S. PATENT DOCUMENTS

| 5,544,664 A | 8/1996 | Benderev et al. |
| 6,099,547 A | 8/2000 | Gellman et al. |
| 2008/0171905 A1* | 7/2008 | Anderson ............... A61F 2/005 600/29 |

FOREIGN PATENT DOCUMENTS

| JP | 9-248306 A | 9/1997 |
| JP | 2001-511686 A | 8/2001 |
| JP | 2010-99499 A | 5/2010 |

OTHER PUBLICATIONS

International Search Report (PCT/ISA/210) mailed on Aug. 28, 2012, by the Japanese Patent Office as the International Searching Authority for International Application No. PCT/JP2012/069684.

* cited by examiner

*Primary Examiner* — Melanie Tyson
(74) *Attorney, Agent, or Firm* — Buchanan Ingersoll & Rooney PC

(57) ABSTRACT

An expansion instrument includes an elongated vaginal-insertion member insertable into the vaginal lumen which is adjacent the urethral lumen with biological tissue interposed between the two, an elongated urethral-insertion member insertable into the urethral lumen, an interlock device interlocking the vaginal-insertion member and the urethral-insertion member to allow the insertion members to be brought closer together and brought farther apart, and a vaginal-side restriction that restricts the positional relationship, with respect to the biological tissue, of the vaginal-insertion member after being inserted into the vaginal lumen. The vaginal-side restriction is on the vaginal-insertion member and has a configuration such that in a state where the vaginal-insertion member is in the vaginal lumen, the urethral-insertion member is in the urethral lumen, and the positional relationship has been restricted by the vaginal-side restriction, moving the vaginal-insertion member far- (Continued)

ther away from the urethral-insertion member widens the biological tissue in the moving away direction.

15 Claims, 15 Drawing Sheets

(51) Int. Cl.
    *A61B 17/02* (2006.01)
    *A61B 17/42* (2006.01)
    *A61F 2/00* (2006.01)
    *A61B 17/00* (2006.01)
    *A61B 17/30* (2006.01)

(52) U.S. Cl.
    CPC .............. *A61B 17/30* (2013.01); *A61B 17/42* (2013.01); *A61F 2/0045* (2013.01); *A61F 2/0063* (2013.01); *A61B 2017/00557* (2013.01); *A61B 2017/00805* (2013.01); *A61B 2017/0225* (2013.01); *A61B 2017/306* (2013.01); *A61F 2002/0072* (2013.01)

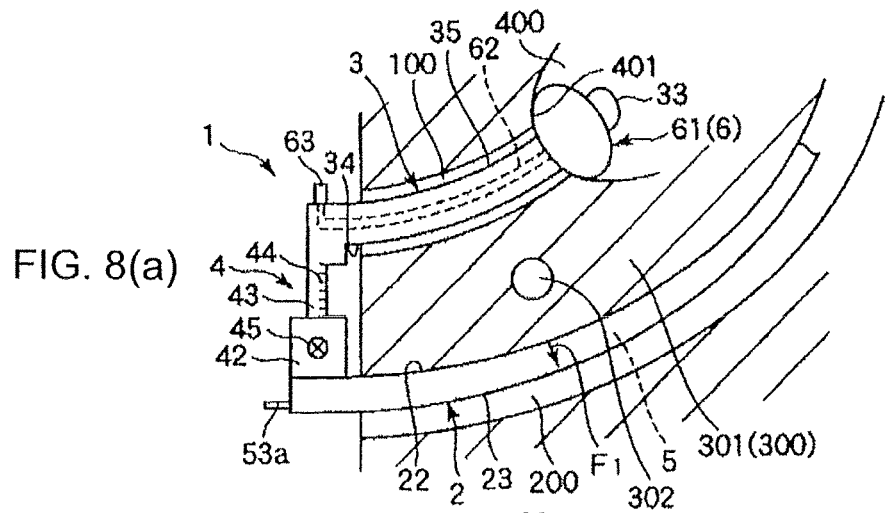
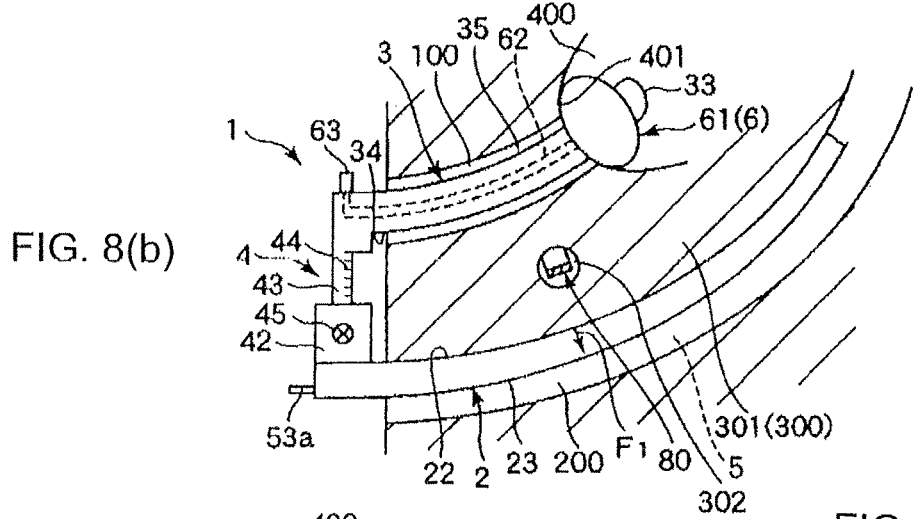
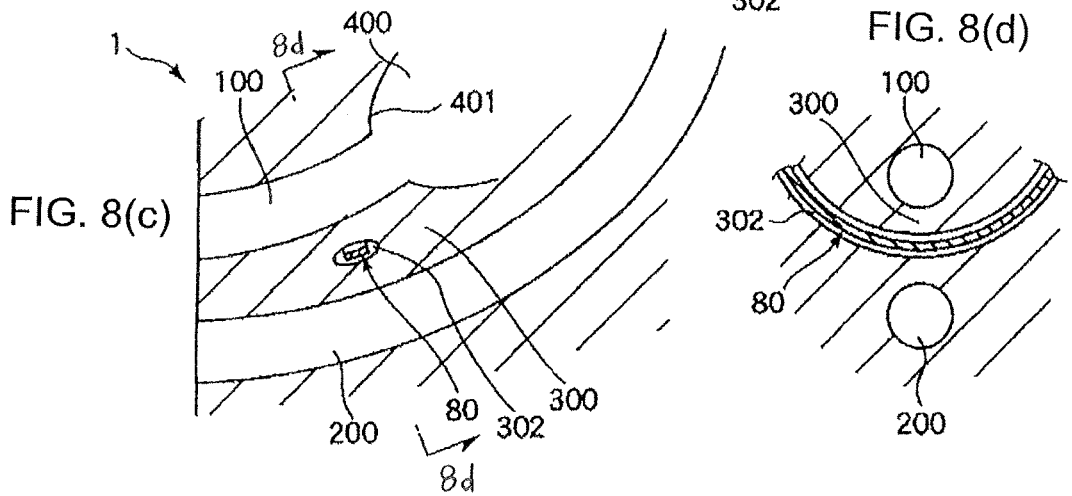

EXPANSION INSTRUMENT

CROSS REFERENCES TO RELATED APPLICATIONS

This application is a continuation of International Application No. PCT/JP2012/069684 filed on Feb. 8, 2012, and claims priority to Japanese Application No. 2011-255412 filed on Nov. 22, 2011, the entire content of both of which is incorporated herein by reference.

TECHNICAL FIELD

The present invention generally relates to an expansion instrument.

BACKGROUND DISCUSSION

In a patient suffering from urinary incontinence, particularly stress urinary incontinence, urine leakage (involuntary urination) occurs due to abdominal pressure exerted during a normal exercise or by laughing, coughing, sneezing or the like. This is attributable, for example, to loosening of the pelvic floor muscle, which is a muscle that supports the urethra, caused by childbirth or the like.

For treatment of urinary incontinence, surgical therapy is effective. For instance, a tape-shaped implant called a "sling" is used and set indwelling in the body so as to support the urethra by the sling. An example is disclosed in Japanese Patent Application Publication No. 2010-99499. To put a sling indwelling in the body, an operator incises the vagina with a surgical knife, dissects biological tissue (living body tissue) between the urethra and the vagina, and provides communication between the dissected biological tissue and the exterior through an obturator foramen by using a puncture needle or the like. Then, in such a state, the sling is set indwelling in the dissected biological tissue in the body.

Since the biological tissue between the urethra and the vagina is a very thin layer, however, an insufficient skill of the operator may lead to damage to the urethra during dissection of the biological tissue. In addition, where the dissected layer of the biological tissue is close to the vagina side, the sling set indwelling may be located excessively close to the vagina side. In such a case, with the lapse of time after the surgery, the sling may come to break through the vaginal wall, to be exposed to the inside of the vagina.

SUMMARY

According to one aspect of the disclosure here, an expansion instrument comprises: an elongated vaginal-insertion member configured to be inserted into a vaginal lumen positioned adjacent a urethral lumen, with biological tissue located between the vaginal lumen and the urethral lumen; an elongated urethral-insertion member configured to be inserted into the urethral lumen; interlock means for interlocking the vaginal-insertion member and the urethral-insertion member and allowing the vaginal-insertion member and the urethral-insertion member to be brought closer together and moved farther apart; and vaginal-side restriction means, provided on the vaginal-insertion member, for restricting a positional relationship, with respect to the biological tissue, of the vaginal-insertion member after the vaginal-insertion member is inserted into the vaginal lumen. In a state in which the vaginal-insertion member is positioned in the vaginal lumen, the urethral-insertion member is positioned in the urethral lumen, and the positional relationship between the vaginal-insertion member and the urethral-insertion member is restricted by operation of the vaginal-side restriction means, moving the vaginal-insertion member in a direction away from the urethral-insertion member widens the biological tissue located between the vaginal lumen and the urethral lumen in the moving away direction.

The expansion instrument helps ensure that, at the time of applying a surgical treatment to a biological tissue between a vaginal lumen (vaginal cavity) and a urethral lumen, the treatment can be carried out rather easily and assuredly.

The vaginal-insertion member can be composed of a plate-shaped member, and the vaginal-side restriction means can include an internal space inside the vaginal-insertion member and at least one suction port communicating with the internal space. The suction port opens to the surface of the vaginal-insertion member that faces the urethral-insertion member, and the vaginal-side restriction means is configured to be connected to suction means applying suction to the internal space such that the vaginal-side restriction means restricts the positional relationship by drawing the biological tissue toward the vaginal-insertion member through a suction force generated at the suction port when the suction means is operated in the connected state.

The at least one suction port can be in the form of a plurality of suction ports arranged in a matrix pattern in plane directions of the surface of the vaginal-insertion member that faces the urethral-insertion member. The suction port can also be configured as a projection projecting toward the urethral-insertion member side from the surface of the vaginal-insertion member that faces the urethral-insertion member. The internal space inside the vaginal-insertion member can be partitioned into a plurality of chambers through walls provided within the internal space.

The vaginal-side restriction means preferably includes at least one pinching mechanism to pinch the biological tissue, and restrict the positional relationship through drawing the biological tissue toward the vaginal-insertion member by a pinching force generated by the pinching mechanism. The pinching mechanism preferably includes a pair of pinching pieces pinching the biological tissue, and a biasing section biasing each of the pinching pieces in a direction to generate the pinching force or a direction for releasing the pinching force.

The interlock means can include a locking mechanism maintaining the distance between the vaginal-insertion member and the urethral-insertion member. The locking mechanism preferably includes a bolt such that tightening the bolt keeps the distance between the vaginal-insertion member and the urethral-insertion member constant and loosening the bolt makes the distance variable.

The interlock means preferably includes graduations identifying the distance between the vaginal-insertion member and the urethral-insertion member.

The expansion instrument preferably also includes urethral-side restriction means restricting a positional relationship, with respect to the biological tissue, of the urethral-insertion member having been inserted into the urethral lumen, wherein the urethral-side restriction means is provided on the urethral-insertion member.

The urethral-insertion member can be composed of a rod-shaped member, and the urethral-side restriction means can include a flow path formed in the inside of the urethral-insertion member. At least one auxiliary suction port communicates with the flow path, wherein the auxiliary suction port open at a surface of the urethral-insertion member that faces the vaginal-insertion member side. The urethral-side restriction means is configured to be connected to suction means applying suction to the inside of the flow path, and the urethral-side restriction means restricts the positional relationship of the urethral-insertion member with respect to the biological tissue through drawing the biological tissue toward the urethral-insertion member by a suction force generated at the auxiliary suction port when the suction means is operated in the connected state.

The vaginal-insertion member is composed of a plate-shaped member, and is provided with a window through which the other major surface side thereof can be visually checked from one major surface side thereof.

The urethral-side restriction means can include a balloon which can be inflated and deflated, and restricts the position of the urethral-insertion member in a longitudinal direction in a state where the balloon has been inflated. In addition, the vaginal-insertion member is preferably curved. The urethral-insertion member is also preferably curved in the same direction as the vaginal-insertion member.

The urethral-insertion member includes a deformation section where a part thereof is deformed, such that when the urethral-insertion member has been inserted into the urethral lumen, the deformation section widens, in a direction for bringing the urethral lumen and the vaginal lumen farther apart, a portion of the urethral lumen that faces the deformation section.

As discussed above, the expansion instrument is configured so that at the time of applying surgical treatment to a biological tissue between the vaginal lumen and the urethral lumen, the treatment can be carried out relatively easily and assuredly. For instance, where the expansion instrument is used for treatment of female urinary incontinence, it is possible, by inserting the vaginal-insertion member of the expansion instrument into the vaginal lumen, inserting the urethral-insertion member into the urethral lumen and operating the vaginal-side restriction means, to establish a state in which the positional relationship of the vaginal-insertion member with the biological tissue is restricted.

In this treatment of urinary incontinence, part of the biological tissue present between the urethral lumen and the vaginal lumen is dissected, and the dissected part and the outside of the body is made to communicate with each other via a puncture hole formed by puncture, for example. Thereafter, an implant for supporting the urethra is set indwelling in the biological tissue, in the puncture hole.

In such a treatment of urinary incontinence, when the vaginal-insertion member is brought away from the urethral-insertion member while maintaining the aforementioned state, the biological tissue is widened in the direction of bringing away. The thus widened part has been widened to a sufficient extent for performing the dissection and the puncture. Therefore, it is ensured that at the time of applying a surgical treatment such as dissection and puncture to the widened part, the treatment can be carried out rather easily and assuredly.

In accordance with another aspect, an expansion instrument comprises: an elongated vaginal-insertion member configured to be inserted into a vaginal lumen positioned adjacent a urethral lumen, with biological tissue located between the vaginal lumen and the urethral lumen; and an elongated urethral-insertion member configured to be inserted into the urethral lumen; wherein the vaginal-insertion member and the urethral-insertion member are adjustably connected to one another to permit adjustment of a spacing between the vaginal-insertion member and the urethral-insertion member. The vaginal-insertion member includes: i) at least one hole communicating with a lumen in the vaginal-insertion member which is connectable to a suction source to hold the biological tissue located between the vaginal lumen and the urethral lumen when the vaginal-insertion member is positioned in the vaginal lumen to positionally restrict the vaginal-insertion member in the vaginal lumen, the at least one hole opening to a surface of the vaginal-insertion member directly facing the urethral-insertion member; and/or ii) a biological tissue holder configured to hold the biological tissue located between the vaginal lumen and the urethral lumen when the vaginal-insertion member is positioned in the vaginal lumen to positionally restrict the vaginal-insertion member in the vaginal lumen.

BRIEF DESCRIPTION OF DRAWINGS

FIGS. 8(a), (b), (c) and (d) are partial longitudinal cross-sectional views sequentially illustrating the method of using the expansion instrument shown in FIG. 1.

DETAILED DESCRIPTION

The expansion instrument disclosed here will be described below in detail with reference to the accompanying drawings illustrating embodiments that represent examples of the disclosed expansion instrument.

Reference is initially made to FIGS. 1-8 illustrating one example of the expansion instrument disclosed here. In the following description, along the longitudinal direction of a vaginal insertion section and a urethral insertion section in FIGS. 1 to 5 (and in FIG. 11, as well), the lower side is referred to as the "distal end," and the upper side as the "proximal end." Along the longitudinal direction of the vaginal insertion section and the urethral insertion section in FIGS. 7 and 8 (and in FIG. 9, as well), the right upper side or left upper side is referred to as the "distal end," and the left lower side or right lower side as the "proximal end."

Figure 1:
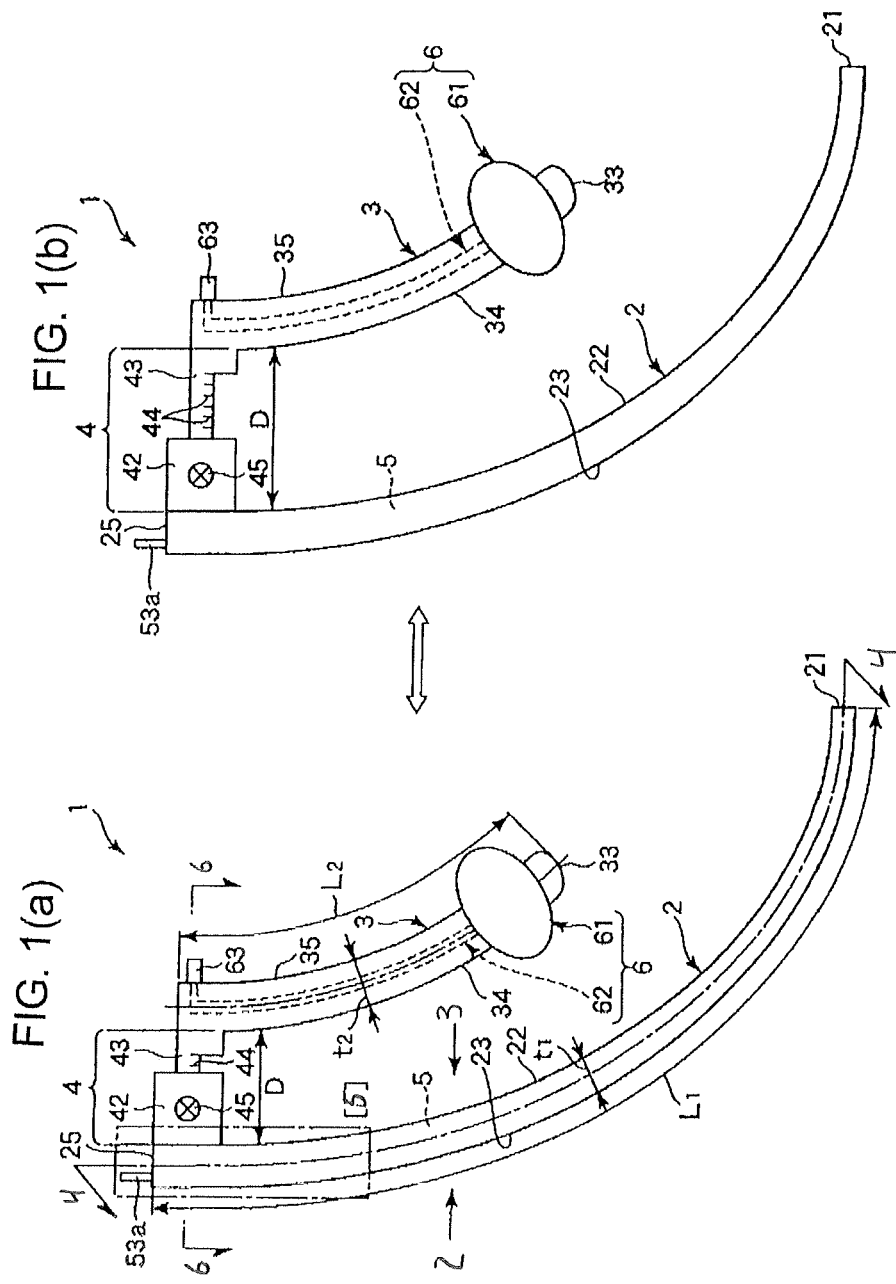
FIGS. 1(a) and 1(b) are side views of an embodiment of an expansion instrument representing an example of the expansion instrument disclosed here in its operating state.

The expansion instrument 1 shown in FIG. 1 is a medical instrument configured to be used by being inserted into a urethral lumen 100 and a vaginal lumen 200, during treatment of female urinary incontinence, specifically, during a process for implanting an implant (an instrument to be set indwelling in a living body) into a living body.

The urethral lumen 100 and the vaginal lumen 200 are adjacent to each other with a biological tissue 300 interposed between the urethral lumen 100 and the vaginal lumen 200 (see FIGS. 7 and 8). The biological tissue 300 includes a wall section (urethral wall) defining the urethral lumen 100, a wall section (vaginal wall) defining the vaginal lumen 200, and the like. In addition, the thickness of this biological tissue 300, in the case of female adults, is said to be about 5 to 20 mm in general, though it varies from individual to individual.

The implant is an instrument to be implanted in the biological tissue 300 to support the urethra in the manner of pulling the urethra away from the vaginal wall, for treatment of female urinary incontinence (see FIGS. 8(c) and 8(d)). In this way, the urethra can be supported, and, therefore, involuntary urination can be prevented.

An example of the implant that can be used include a flexible elongated body. In this embodiment, the implant is composed of a belt 80. The belt 80 is called a "sling."

The dimensions of the belt 80 are not particularly limited but are set as required. The belt 80 is preferably about 3 to 15 mm in width, and preferably about 0.2 to 2 mm in thickness.

The material constituting the belt 80 is not specifically restricted; for instance, various resin materials and the like which are biocompatible can be used as the material.

Note that the implant is composed of a single belt 80 in this embodiment, but is not limited in this way; for example, the implant may be composed of a plurality of belts 80.

The implant is also not restricted to the belt 80. For instance, other flexible elongated bodies such as strings or cords can be used as the implant. In the case where a string or cord is used as the implant and where the implant is circular in cross-sectional shape, the implant's outer diameter is preferably about 0.2 to 5 mm.

As shown in FIG. 1, the expansion instrument 1 includes: an elongated vaginal-insertion member 2 having an elongated shape that is inserted into a vaginal lumen 200; an elongated urethral-insertion member 3 having an elongated shape that is inserted into a urethral lumen 100; interlock means 4 for interlocking or connecting the vaginal-insertion member 2 and the urethral-insertion member 3; vaginal-side restriction means 5 provided on the vaginal-insertion member 2; and urethral-side restriction means 6 provided on the urethral-insertion member 3. The configuration of each of these components is described below.

The shape of the vaginal-insertion member 2 is not specifically restricted, insofar as it is an elongated shape. As shown in FIGS. 1 to 4, the vaginal-insertion member 2 is plate-shaped in this embodiment. While the whole length $L_1$ of the vaginal-insertion member 2 is not particularly limited, it is preferably, for example, 50 to 100 mm, more preferably 60 to 90 mm.

The width $W_1$ of the vaginal-insertion member 2 gradually decreases along the distal direction. While the width $W_1$ (average) is not specifically limited, it is preferably, for example, 10 to 35 mm, more preferably 15 to 30 mm.

The thickness $t_1$ of the vaginal-insertion member 2 also gradually decreases along the distal direction. While the thickness $t_1$ (average) is not particularly limited, it is preferably, for example, 2 to 10 mm, more preferably 4 to 8 mm.

Figure 2:
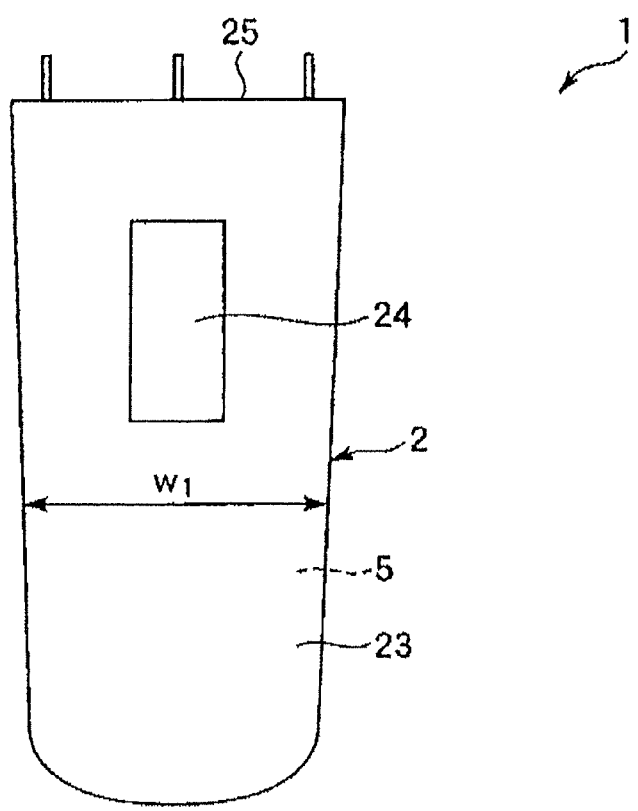
FIG. 2 is a view of the expansion instrument as seen from the direction of the arrow 2 in FIG. 1(a).
Figure 3:
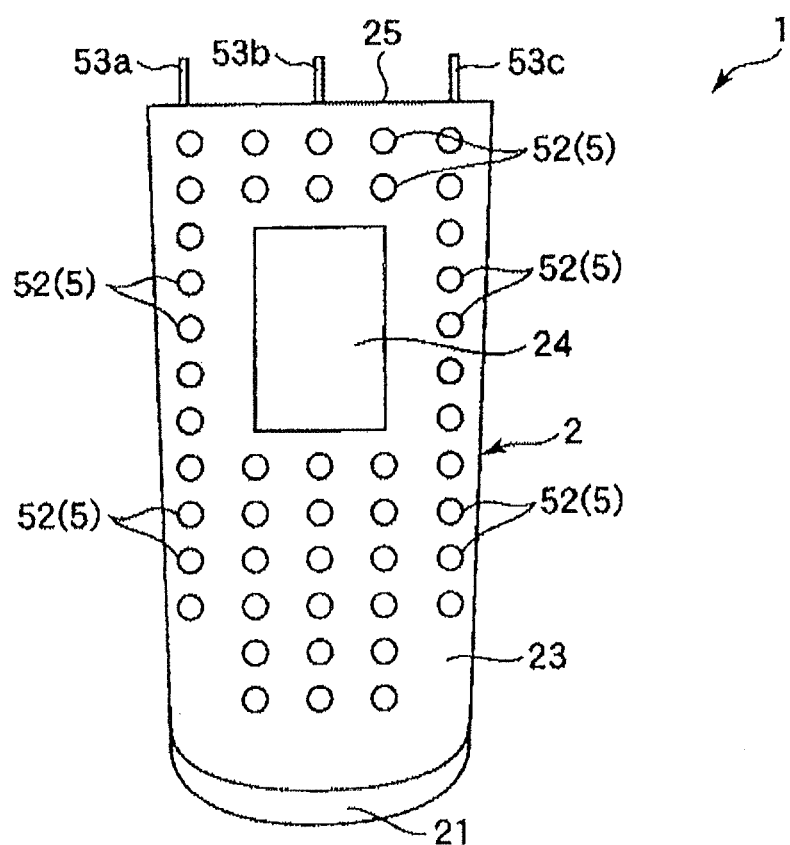
FIG. 3 is a view of the expansion instrument as seen from the direction of the arrow 3 in FIG. 1(a).
Figure 4:
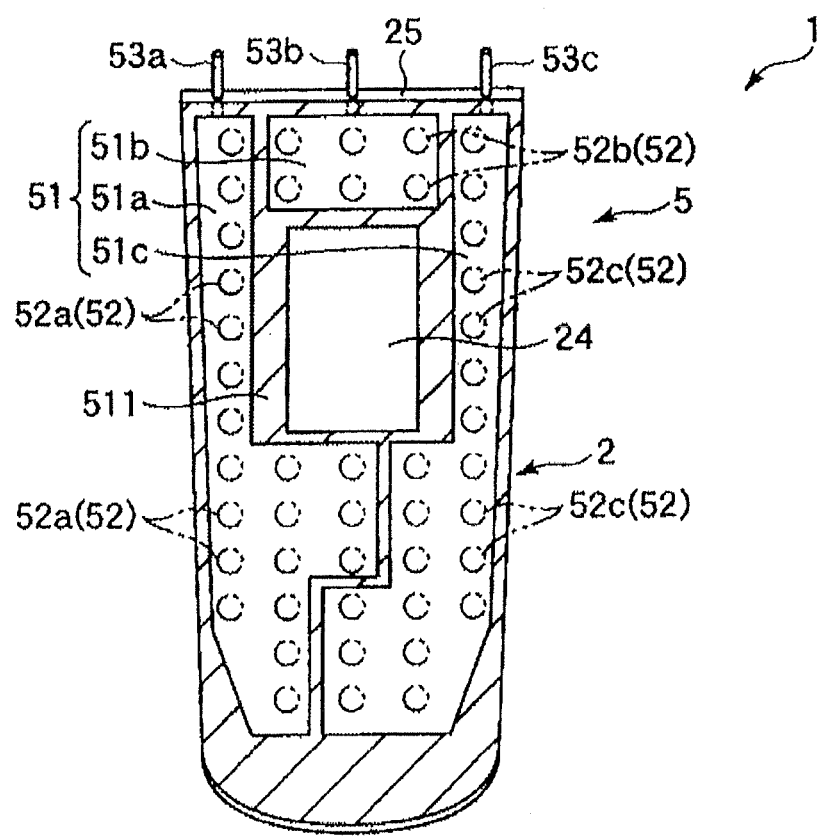
FIG. 4 is a cross-sectional view of the expansion instrument taken along the section line 4-4 in FIG. 1(a).

As shown in FIGS. 2 to 4, the vaginal-insertion member 2 includes a window 24 composed of a through-hole passing through the vaginal-insertion member 2 in the thickness direction of the vaginal-insertion member 2. The window 24 is a part through which the vaginal wall on the side of a surface (other-side surface) 22 on the inside of curvature of the vaginal-insertion member 2 can be visually checked or observed from the side of a surface (one-side surface) 23 on the outside of curvature of the vaginal-insertion member 2. In addition, the window 24 is a part through which treatments or operations such as puncture and incision can be performed.

As shown in FIG. 3, the distal end 21 of the vaginal-insertion member 2 is rounded. This helps ensure that at the time of inserting the vaginal-insertion member 2 into the vaginal lumen 200, the biological tissue 300 and the like can be reliably prevented from being damaged by the distal end 21. Consequently, safety of the vaginal-insertion member 2 for the patient can be enhanced.

As shown in FIG. 1, the vaginal-insertion member 2 is curved in one direction into an arcuate shape, or bowlike shape, in side view. This helps ensure that when the vaginal-insertion member 2 is inserted into the vaginal lumen 200 with the surface 22 on the inside of the curvature of the vaginal-insertion member 2 kept facing the front side of the patient, the vaginal lumen 200 can be widened and the operational field can be oriented toward the front side of the operator. Consequently, visual checking through the window 24 is facilitated, and such treatment as puncture or incision can be facilitated. The curvature of the vaginal-insertion member 2 is not specifically restricted, since a suitable range of curvature varies depending on the patient's position. For instance, the curvature in terms of radius of curvature is preferably 60 to 240 mm. Note that in the case where a transvaginal treatment such as puncture and incision is not frequently performed, the operational field need not be oriented toward the front side of the patient. In such a case, therefore, the vaginal-insertion member 2 may not necessarily be curved, and may be rectilinear in shape.

On the inside of the curvature of the vaginal-insertion member 2 is disposed the urethral-insertion member 3. That is, the concave surface of the vaginal-insertion member 2 faces the urethral-insertion member 3. The shape of the urethral-insertion member 3 is not specifically restricted, insofar as it is an elongated shape. In this embodiment, the urethral-insertion member 3 is rod-shaped, and, further, it is curved in the same direction as the vaginal-insertion member 2. The whole length $L_2$ of the urethral-insertion member 3 is preferably, for example, 50 to 80 mm, more preferably 50 to 60 mm.

In order that the urethral-insertion member 3 and the vaginal-insertion member 2 extend along substantially parallel curved lines, the curvature of the urethral-insertion member 3 is set to have a smaller radius of curvature, as compared to the curvature of the vaginal-insertion member 2.

Since the urethral-insertion member 3 and the vaginal-insertion member 2 are curved to the same direction and to comparable extents, an operation of inserting the urethral-insertion member 3 into a urethral lumen 100 and an operation of inserting the vaginal-insertion member 2 into a vaginal lumen 200 can be carried out en bloc (together and simultaneously) readily. In addition, there is the merit that damage to the urethral wall or the vaginal wall attendant on friction or pressing can be minimized.

The urethral-insertion member 3 is so shaped that its width $w_2$ and thickness $t_2$ are constant along the longitudinal direction. The width $w_2$ is not particularly limited, and is preferably, for example, 2 to 7 mm, more preferably 3 to 6 mm. The thickness $t_2$ is also not specifically limited, and is preferably, for example, 2 to 7 mm, more preferably 2 to 5 mm. When the width $w_2$ of the urethral-insertion member 3 is greater than the thickness $t_2$ of the urethral-insertion member 3, the urethral lumen 100 is deformed into such a shape that the urethral wall is expanded more largely in the widthwise direction, which leads to the merit that at the time of moving the urethral-insertion member 3 and the vaginal-insertion member 2 farther apart by the interlock means 4 (described later), the urethral-insertion member 3 and the urethral wall are not liable to be brought farther apart. In view of this, it is preferable that the width $w_2$ of the urethral-insertion member 3 is greater than the thickness $t_2$ of the urethral-insertion member 3 in such a range as not to hinder the insertion into the urethral lumen 100.

In addition, the distal end 33 of the urethral-insertion member 3 is rounded. This helps ensure that at the time of inserting the urethral-insertion member 3 into the urethral lumen 100, the biological tissue 300 and the like can be securely prevented from being damaged by the distal end 33. Consequently, safety of the urethral-insertion member 3 for the patient can be enhanced.

Figure 6:
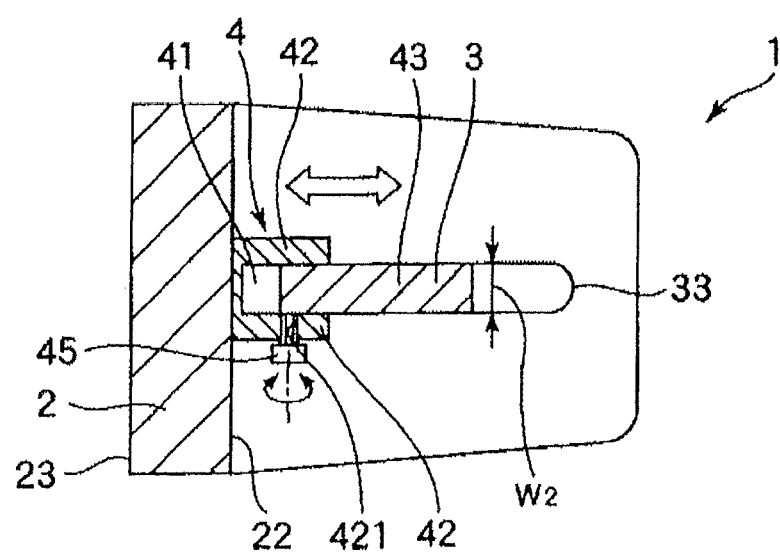
FIG. 6 is a cross-sectional view of the expansion instrument taken along the section line 6-6 in FIG. 1(a).

As shown in FIG. 1, the interlock means 4 is means for interlocking the proximal portions of the vaginal-insertion member 2 and the urethral-insertion member 3 so as to permit these members to be brought closer together and moved farther apart. In this embodiment disclosed by way of example, the interlock means 4 is configured so that the vaginal-insertion member and the urethral-insertion member are adjustably connected to one another to permit adjustment of the spacing or distance between the vaginal-insertion member and the urethral-insertion member. FIG. 6 shows that the interlock means 4 includes a pair of small pieces 42 formed at the surface 22 on the inside of curvature of the vaginal-insertion member 2 so as to project toward the urethral-insertion member 3 side, and a single elongated projection 43 formed at the surface 34 on the outside of the curvature of the urethral-insertion member 3 so as to project toward the vaginal-insertion member 2. The projection 43 is inserted into a gap 41 between the pair of small pieces 42, whereby the projection 43 is supported so as to be slidable in the longitudinal direction of the projection 43. With the projection 43 moved relative to the gap 41, or with the projection 43 retracted into or protruded from the gap 41, the vaginal-insertion member 2 and the urethral-insertion member 3 can be brought closer together or farther away. As a result, the distance D between the surface 22 on the inside of curvature of the vaginal-insertion member 2 and the surface 34 on the outside of curvature of the urethral-insertion member 3 is varied. Therefore, in the interlock means 4, the pair of small pieces 42 and the projection 43 function also as adjustment means for adjusting the distance D. Since patients have individual differences and the thickness of the biological tissue 300 between the urethral lumen 100 and the vaginal lumen 200 may vary from patient to patient, the adjustment means offers the advantage that the distance D between the vaginal-insertion member 2 and the urethral-insertion member 3 can be adjusted according to the patient to be treated.

The range of adjustment of the distance D is preferably, for example, 5 to 35 mm, in order that the distance D conforms to the thicknesses of the biological tissue 300 and an expanded portion 301 (see FIG. 7) enlarged in thickness.

The projection 43 is provided with graduations 44 indicative of the distance D. This permits accurate grasping of the distance D.

The expansion instrument 1 has a bolt (male screw) 45. As shown in FIG. 6, the bolt 45 makes screw engagement with a female screw 421 formed in one 42 of the pair of small pieces 42.

With the bolt 45 rotated in a predetermined direction, specifically, with the bolt 45 tightened, the distal end of the bolt 45 comes into secure contact with the projection 43, whereby the projection 43 is inhibited from moving (i.e., is fixed in position) relative to the small pieces 42. As a result, the distance D can be set at a desired value and kept constant or fixed by operating the bolt 45.

On the other hand, with the bolt 45 rotated in the opposite direction to the above, namely, with the bolt 45 loosened, the distal end of the bolt 45 is spaced apart from the projection 43, whereby the projection 43 is permitted to move relative to the small pieces 42. Consequently, the distance D becomes variable.

Thus, the interlock means 4 is composed of the bolt (male screw) 45 and the female screw 421 formed in the small piece 42, and has a locking function for keeping the distance D constant.

Note that in a state where the bolt 45 has been loosened, the projection 43 is releasable from the pair of small pieces 42. Therefore, the projection 43 can be interlocked to the pair of small pieces 42 after the vaginal-insertion member 2 and the urethral-insertion member 3 are independently inserted into the vaginal lumen 200 and the urethral lumen 100. In addition, in the case where the dimensions of the vaginal-insertion member 2 or the urethral-insertion member 3 do not conform to the size of the vaginal lumen 200 or the urethral lumen 100 of the patient, it is possible to once pulling out only the relevant insertion member and thereafter insert one having different dimensions, in other words, it is possible to selectively exchange only one of the insertion members.

The materials constituting the components of the interlock means 4, the vaginal-insertion member 2 and the urethral-insertion member 3 are not specifically restricted. Examples of applicable materials include various metallic materials such as aluminum, aluminum alloys, stainless steel, etc. and various resin materials.

Figure 5:
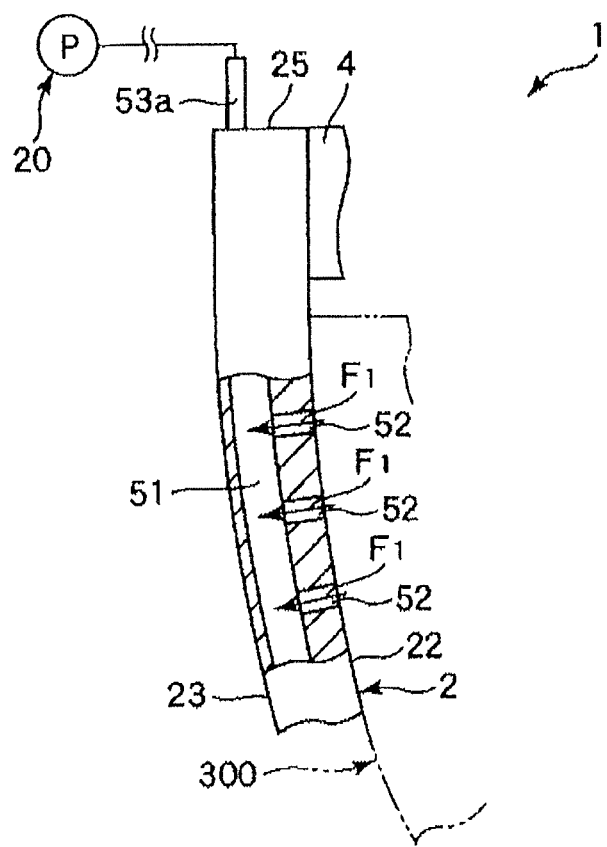
FIG. 5 is an enlarged detailed partial longitudinal cross-sectional view of the region "5" surrounded by the dot-dash line in FIG. 1(a).

The vaginal-side restriction means 5 is means for restricting the positional relationship, with respect to the biological tissue 300, of the vaginal-insertion member 2 after the vaginal-insertion member 2 has been inserted into the vaginal lumen 200. As shown in FIGS. 3 to 5, the vaginal-side restriction means 5 includes: an internal space 51 in the inside of the vaginal-insertion member 2; a plurality of suction ports 52 opening at the surface 22 on the inside of the curvature (the surface facing the urethral-insertion member 3) of the vaginal insertion member 2; and bolts 53a, 53b, and 53c projecting from a proximal end face 25 of the vaginal-insertion member 2.

As shown in FIG. 4, the internal space 51 is partitioned into a plurality of chambers (chambers 51a, 51b, and 51c) through walls 511 provided within the internal space 51. The chamber 51a is disposed on the left side in FIG. 4, the chamber 51c is disposed on the right side in FIG. 4, and the chamber 51b is disposed between the chamber 51a and the chamber 51c and on the upper side in FIG. 4.

As shown in FIG. 3, the plurality of suction ports 52 are arranged in a matrix pattern in plane directions of the surface 22 on the inside of curvature of the vaginal-insertion member 2 (i.e., on the surface of the vaginal-insertion member 2 directly facing the urethral-insertion member 3), in such a manner as to surround the window 24. In addition, as shown in FIG. 4, these suction ports 52 include: suction ports which communicate with the chamber 51*a* (hereinafter, these suction ports will be referred to as "suction ports 52*a*"); suction ports which communicate with the chamber 51*b* (hereinafter, these suction ports will be referred to as "suction ports 52*b*"); and suction ports which communicate with the chamber 51*c* (hereinafter, these suction ports will be referred to as "suction ports 52*c*").

The ports 53*a*, 53*b*, and 53*c* are each composed of a tubular body. The port 53*a* communicates with the chamber 51*a*, the port 53*b* communicates with the chamber 51*b*, and the port 53*c* with the chamber 51*c*. As shown in FIG. 5, the ports 53*a*, 53*b*, and 53*c* are connected respectively to pumps 20 (suction means for applying suction) by which suction can be applied to the three chambers 51*a*, 51*b*, and 51*c* (the internal space 51) independently and respectively. The pumps 20 can be operated in the connected state. In this instance, a suction force (the same suction force) $F_1$ is generated at each suction port 52. By the suction forces $F_1$, the biological tissue 300 is drawn toward the vaginal-insertion member 2 to make secure contact with the surface 22 on the inside of curvature of the vaginal-insertion member 2. As a result, the vaginal-insertion member 2 having been inserted into the vaginal lumen 200 is assuredly restricted in the positional relationship, with respect to the biological tissue 300, of the surface 22 on the inside of curvature thereof. Specifically, the vaginal-insertion member 2 is positioned in any of the lengthwise direction, widthwise direction and thickness direction of the vaginal-insertion member 2, so that the vaginal-insertion member 2 is securely prevented from coming off the restricted position.

Here, in the case where during operation of the pump(s) 20 one or some suction ports 52*a* of the plurality of suction ports 52*a* should be spaced apart from the biological tissue 300 due, for example, to the patient's abrupt motion, the chamber 51*a* would communicate with the atmosphere through the spaced-apart suction port(s) 52*a*, namely, be released to the atmosphere, whereby air-tightness would be spoiled, and the suction forces $F_1$ at the suction ports 52*a* might probably be lowered. In the expansion instrument 1, however, since the chambers 51*a*, 51*b*, and 51*c* are kept independent from each other by the walls 511, even leakage of air in regard of the chamber 51*a* does not break the air-tightness of the remaining chambers 51*b* and 51*c*. This helps ensure that the suction force $F_1$ at each of the suction ports 52*b* communicating with the chamber 51*b* and the suction force $F_1$ at each of the suction ports 52*c* communicating with the chamber 51*c* are securely prevented from being lowered. Accordingly, the positional relationship of the vaginal-insertion member 2 with the biological tissue 300 can be restricted (fixed) in a sufficient manner.

While the number of the partitioned chambers within the internal space 51 is three in this illustrated embodiment disclosed by way of example, this is not restrictive. For example, the number of partitioned chambers may be one, two or more than three.

In addition, while the number of the suction port(s) 52 formed to communicate with each chamber is plural in this embodiment, this is not restrictive; for example, the number may be one.

The number of the ports arranged to be connected to the pumps 20 is three in this embodiment, this is not limitative; for example, the number may be one, two or more than three.

The urethral-side restriction means 6 is means for restricting the positional relationship, with respect to the biological tissue 300, of the urethral-insertion member 3 having been inserted into the urethral lumen 100. As shown in FIG. 1, the urethral-side restriction means 6 includes: an inflatable and deflatable balloon 61 disposed at a distal portion of the urethral-insertion member 3; a lumen 62 located inside the urethral-insertion member 3 and constituting a flow path for passage therethrough of a working fluid for inflation and deflation of the balloon 61; and a port 63 communicating with the lumen 62, the port 63 being formed to project from the surface 35 on the inside of the curvature of the urethral-insertion member 3.

The balloon 61 is composed of a hollow cylindrically shaped film. The balloon 61 is disposed by having its proximal portion and distal portion respectively secured to an outer circumferential surface of the urethral-insertion member 3 in an air-tight manner. The lumen 62 has its distal portion opening into the balloon 61. When the balloon 61 is supplied with the working fluid through the lumen 62, the balloon 61 is inflated into a ball-like shape, for example. At the time of use of the expansion instrument 1, the balloon 61 is inserted into the patient's bladder 400, and is caught on the bladder neck 401 in the inflated state. This makes it possible to restrict the position in the longitudinal direction of the urethral-insertion member 3, relative to the biological tissue 300. Consequently, the urethral-insertion member 3 can be securely prevented from being unwillingly drawn out of the urethral lumen 100.

The method for securing the balloon 61 to the urethral-insertion member 3 is not particularly limited. Examples of the method applicable here include fusion methods (thermal fusion, high-frequency fusion, ultrasonic fusion, etc.), and adhesion methods (adhesion by use of an adhesive or a solvent).

The material constituting the balloon 61 is not specifically limited. Examples of the applicable material include polyester resins such as polyethylene terephthalate, polyethylene naphthalate, polybutylene terephthalate, polybutylene naphthalate, etc. or polyester elastomers containing the polyester resins; olefin resins such as polyethylene, polypropylene, etc. or cross-linked products thereof (particularly, those cross-linked by irradiation with electron beams); polyamide resins such as nylon 11, nylon 12, nylon 610, etc. or polyamide elastomers containing the polyamide resins; polyurethane resins; ethylene-vinyl acetate copolymer or cross-linked products thereof; and polymer blends, polymer alloys and the like containing at least one of these resin materials.

The lumen 62 is so formed as to pass through the urethral-insertion member 3. As aforementioned, the distal portion of the lumen 62 opens into the balloon 61, whereas a proximal portion of the lumen 62 opens in the surface 35 on the inside of curvature of the urethral-insertion member 3.

In addition, the port 63 is composed of a tubular body, and communicates with the lumen 62. To the port 63 can be connected a balloon inflation instrument such as, for example, a syringe. In the connected state, the balloon inflation instrument is operated so that a working fluid supplied through the balloon inflation instrument is sent into the inside of the balloon 61 or is drawn out of the balloon 61, through the lumen 62, whereby the balloon 61 is inflated or deflated. Examples of the working fluid for inflation of the balloon include liquids such as physiological saline solution, gases such as air, and the like. Like a balloon inflation port of a commercially available ordinary urethral catheter (Foley catheter), the port 63 is preferably provided with a valve element that opens a flow path only when a balloon inflation instrument such as a syringe is connected.

Now, one example of the method of using the expansion instrument 1, specifically, the procedure for implanting the belt 80 into a living body for the purpose of treating female urinary incontinence, will be described referring to FIGS. 7 and 8.

[1] First, the expansion instrument 1 is prepared. In this instance, in the expansion instrument 1, the balloon 61 has not yet been inflated; that is, the balloon 61 is in a deflated state. In addition, a syringe preliminarily filled with physiological saline solution is also prepared. The physiological saline solution is used as a working fluid for actuating the balloon 61.

Figure 7A:
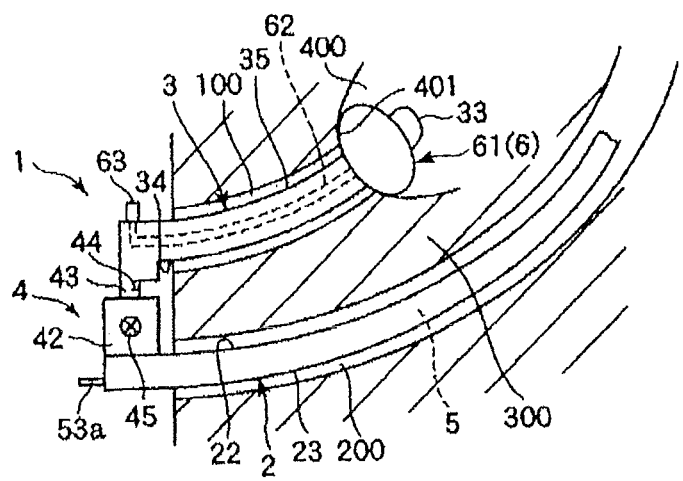
FIGS. 7(a), 7(b) and 7(c) are partial longitudinal cross-sectional views sequentially illustrating a method of using the expansion instrument shown in FIGS. 1(a) and 1(b).

Then, as shown in FIG. 7(a), the expansion instrument 1 is mounted to the patient. To be more specific, the vaginal-insertion member 2 of the expansion instrument 1 is inserted into the vaginal lumen 200, and the urethral-insertion member 3 is inserted into the urethral lumen 100. This insertion is carried out until the balloon 61 (deflated balloon) is positioned in the bladder 400.

At the time of this insertion, if necessary, the interlock means 4 is operated to adjust the distance between the vaginal-insertion member 2 and the urethral-insertion member 3. In other words, if necessary, the bolt 45 is rotated in the loosening direction, thereby to bring the vaginal-insertion member 2 and the urethral-insertion member 3 closer together or farther apart. In this case, the distance D is adjusted to such an extent that the vaginal-insertion member 2 is insertable into the vaginal lumen 200 and the urethral-insertion member 3 is insertable into the urethral lumen 100. After the adjustment of the distance D, the bolt 45 is rotated in the tightening direction, to once keep the distance D. AS described above, it is also possible to preliminarily rotate the bolt 45 in the loosening direction, then insert the vaginal-insertion member 2 and the urethral-insertion member 3 into the vaginal lumen 200 and the urethral lumen 100 in an independent manner, and thereafter interlock the projection 43 and the pair of small pieces 42.

Subsequently, the syringe is connected to the port 63 provided in the urethral-insertion member 3, and the syringe is operated to supply the physiological saline solution into the lumen 62. This results in inflation of the balloon 61, so that the inflating balloon engages the bladder neck 401 of the bladder 400. As a result, the position in the longitudinal direction of the urethral-insertion member 3 relative to the urethral lumen 100 is restricted, and, accordingly, the urethral-insertion member 3 is prevented from being drawn-out (axially drawn-out) of the urethral lumen 100 unwillingly.

The ports 53a to 53c provided in the vaginal-insertion member 2 and the pumps 20 are connected to each other. In this case, the pumps 20 are still in a stopped state. That is, suction is not applied to the ports 53a to 53c.

Figure 7B:
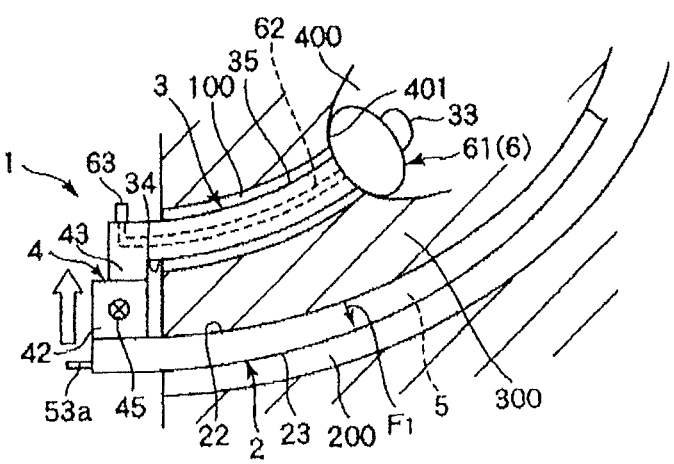

[2] Next, as shown in FIG. 7(b), the bolt 45 is again loosened, and the vaginal-insertion member 2 is brought closer to the urethral-insertion member 3 until the surface 22 on the inside of the curvature of the vaginal-insertion member 2 (i.e., the surface of the vaginal-insertion member 2 facing the urethral-insertion member 3) comes into contact with the biological tissue 300.

Thereafter, the pumps 20 are operated. This causes the suction force $F_1$ to be generated at each of the suction ports 52 formed in the vaginal-insertion member 2, as described above, whereby the positional relationship of the vaginal-insertion member 2 with the biological tissue 300 is securely restricted.

Figure 7C:
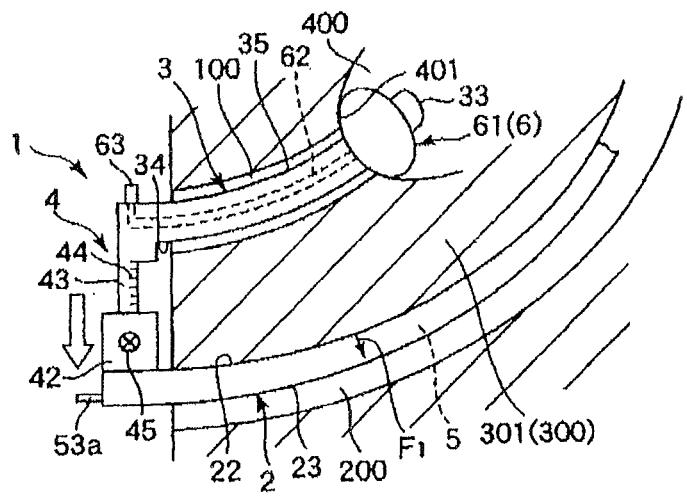

[3] Next, as shown in FIG. 7(c), the vaginal-insertion member 2 is gradually brought farther away from the urethral-insertion member 3. In this instance, owing to the suction forces $F_1$ (the vaginal-side restriction means 5), the vaginal-insertion member 2 is maintained in contact with the biological tissue 300 and is securely prevented from coming apart from the biological tissue 300.

Then, by virtue of this bringing-away or moving-away operation shown in FIG. 7(c), the biological tissue 300 is forcibly pulled (corrected) in the operating direction (the direction of bringing away). As a result, the biological tissue 300 becomes the expanded portion 301 which is widened or enlarged in thickness relative to before the moving-away in such a direction that the urethral lumen 100 and the vaginal lumen 200 are brought farther away from each other (the distance between the urethral lumen 100 and the vaginal lumen 200 increases).

[4] Subsequently, as shown in FIG. 8(a), the expanded portion 301 is dissected, and a puncture hole 302 for providing communication between the dissected expanded portion 301 and the outside of the body is formed, by use of a surgical knife (not shown) and a puncture needle (not shown). The expanded portion 301 to which the dissection operation and the puncturing operation are applied has been expanded to an extent sufficient for these operations to be conducted. Accordingly, at the time of applying the surgical treatment (in this embodiment, the dissection operation and the puncturing operation) to the expanded portion 301 by use of the expansion instrument 1, the treatment can be carried out rather easily and assuredly.

[5] Next, as shown in FIG. 8(b), the belt 80 is passed through the puncture hole 302 by use of a guide wire, for example. The belt 80 is in the state of having both its end portions protruding from the puncture hole 302 to the exterior of the body, with the urethral wall (the expanded portion 301) hooked by the belt 80.

[6] Subsequently, as shown in FIG. 8(c), the expansion instrument 1 is detached from the patient. Specifically, the vaginal-insertion member 2 of the expansion instrument 1 is pulled out of the vaginal lumen 200, and the urethral-insertion member 3 of the expansion instrument 1 is pulled out of the urethral lumen 100. At the time of this pulling-out operation, operation of the pumps 20 is stopped, and the balloon 61 is deflated. When the expansion instrument 1 is detached from the patient, the expanded portion 301 of the biological tissue 300 disappears, namely, the biological tissue 300 is restored to its original state (original shape).

Then, both end portions of the belt 80 which are protruding to the outside of the body are pulled with predetermined forces, respectively. This helps ensure that the urethral wall is pulled away from the vaginal wall by the tension on the belt 80, and the urethra is supported by the belt 80 (see FIG. 8(g)).

Thereafter, unrequired portions of the belt 80 are cut away, and predetermined operations such as closure of incision are conducted, to complete the surgical procedure.

While the use of the expansion instrument 1 at the time of implanting into a living body an implant capable of being implanted for treatment of female urinary incontinence has been described in this embodiment, this is not restrictive, and the expansion instrument 1 can be applied to other uses, such as treatment of diseases in pelvic organs, inclusive of pelvic organ prolapse.

Figure 9:
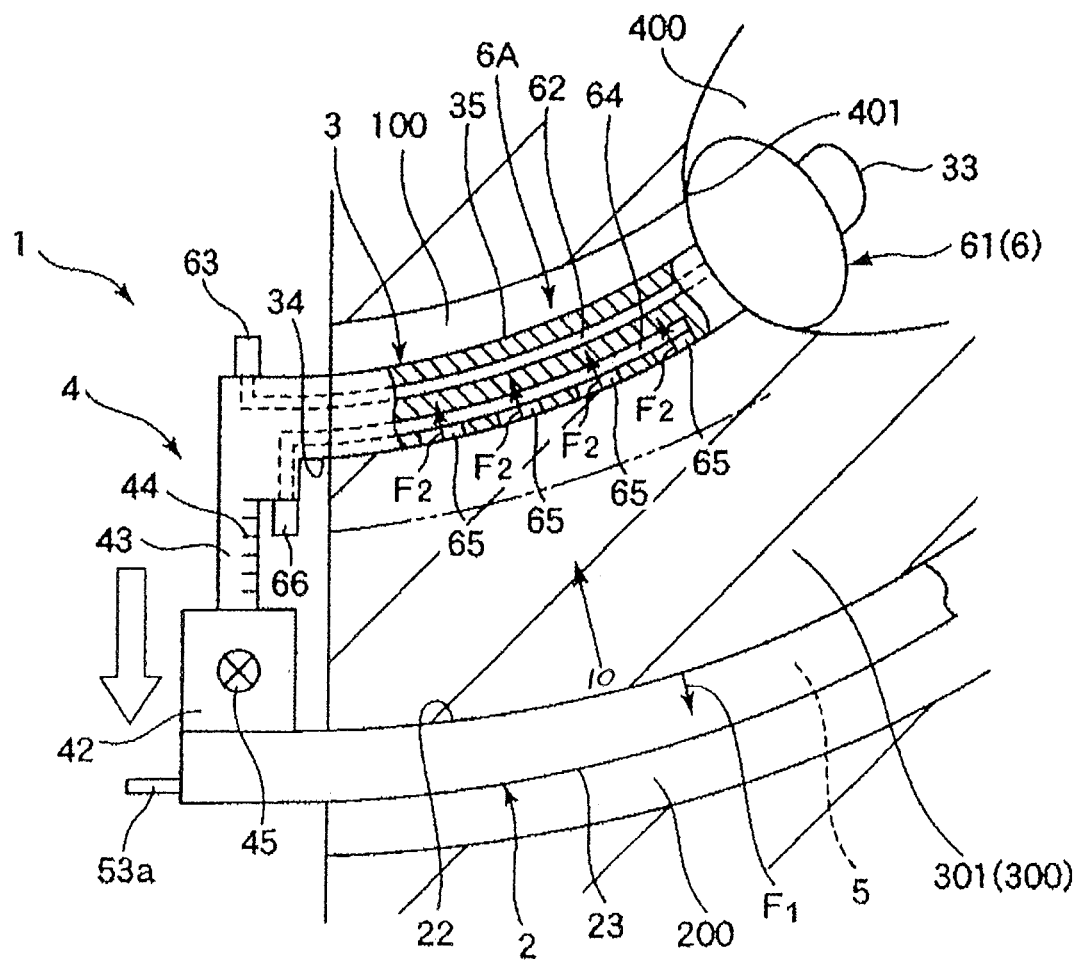
FIG. 9 is an illustration of another embodiment of the expansion instrument disclosed here in its state in use.
Figure 10:
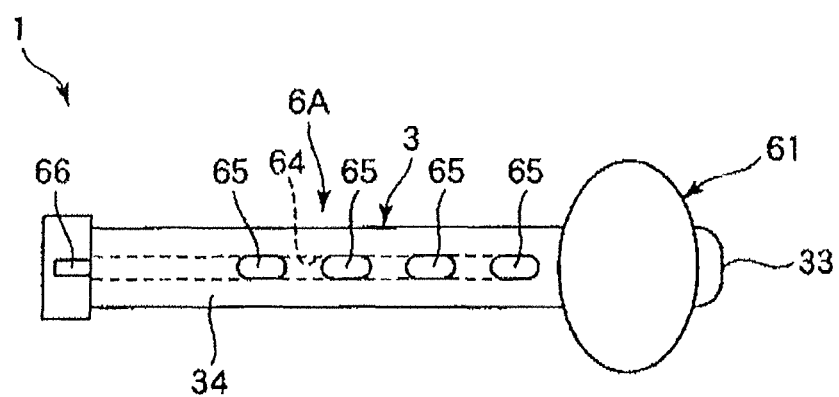
FIG. 10 is a view along the arrow 10 in FIG. 9.

FIGS. 9 and 10 illustrate a second embodiment of an expansion instrument representing another example of the disclosed expansion instrument. The following description focuses primarily on differences between this embodiment of the expansion instrument and the embodiment described above. Features of this second embodiment of the expansion instrument that are the same as in the first embodiment are identified by common reference numerals and a detailed description of such features is not repeated.

This second embodiment of the expansion instrument is the same as the first embodiment, except for a difference in the configuration of the urethral-side restriction means.

As shown in FIGS. 9 and 10, in this embodiment, urethra-side restriction means 6A of the expansion instrument 1 further includes: a lumen 64 inside the urethral-insertion member 3 independently from the lumen 62, wherein the lumen 64 constitutes a flow path for passage of air through the lumen 64; a plurality of (in this embodiment, four) auxiliary suction ports 65 which open at (communicate with) the surface 34 on the outside of the curvature (the surface facing the vaginal-insertion member 2 side) of the urethral-insertion member 3, and which communicate with the lumen 64; and a port 66 which protrudes from the urethral-insertion member 3 and communicates with the lumen 64.

The lumen 64 passes through the urethral-insertion member 3.

The auxiliary suction ports 65 are arranged along the direction in which the lumen 64 extends (the longitudinal direction of the urethral-insertion member 3).

The port 66 is composed of a tubular body, and communicates with the lumen 64. To the port 66 is connected a pump 20, for example. With the pump 20 operated in this connected state, suction is applied to the inside of the lumen 64. In this case, a suction force $F_2$ is generated at each of the auxiliary suction ports 65. The suction forces $F_2$ cause the biological tissue 300 to be drawn toward the surface 34 to make secure contact with the surface 34 on the outside of the curvature of the urethral-insertion member 3. As a result, the urethral-insertion member 3 having been inserted into the urethral lumen 100 is assuredly restricted (fixed) in the positional relationship, with respect to the biological tissue 300, of the surface 34 on the outside of curvature thereof. Specifically, the urethral-insertion member 3 is positioned in any of the lengthwise direction, widthwise direction and thickness direction of the urethral-insertion member 3, so that the urethral-insertion member 3 is securely prevented from coming off the restricted position.

When the vaginal-insertion member 2 is brought-away or moved-away from the urethral-insertion member 3 while keeping the vaginal-side restriction means 5 in operation, and if, for example, the bringing-away or moving-away speed is too high or the bringing-away or moving-away distance is too long, the portion of the biological tissue 300 that defines the urethral lumen 100 would also be pulled in that direction (see the part indicated by two-dot chain line in FIG. 9). As a result, it seems that the expanded portion 301 might not be formed in the biological tissue 300. In this embodiment, however, such unwilling deformation of the biological tissue 300 due to an excessive pulling of the biological tissue 300 can be securely prevented or restricted by the suction force $F_2$ at each of the auxiliary suction ports 65. As a result, the expanded portion 301 can be formed more assuredly.

While the number of auxiliary suction port(s) 65 formed is four in this embodiment, this is not restrictive; for example, the number may be one, two, three or more than four.

Figure 11:
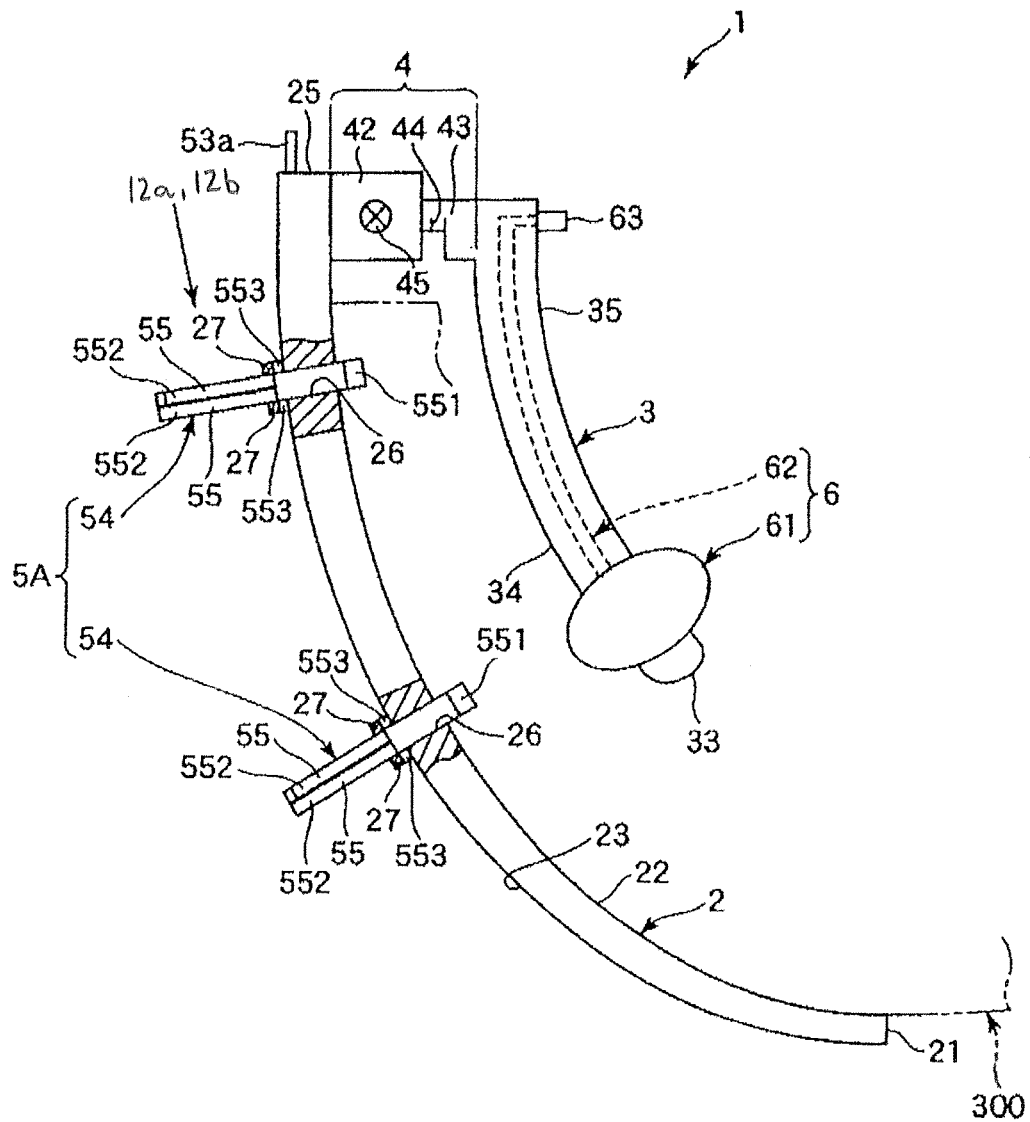
FIG. 11 is a side view of a third embodiment of an expansion instrument disclosed here.
Figure 12A:
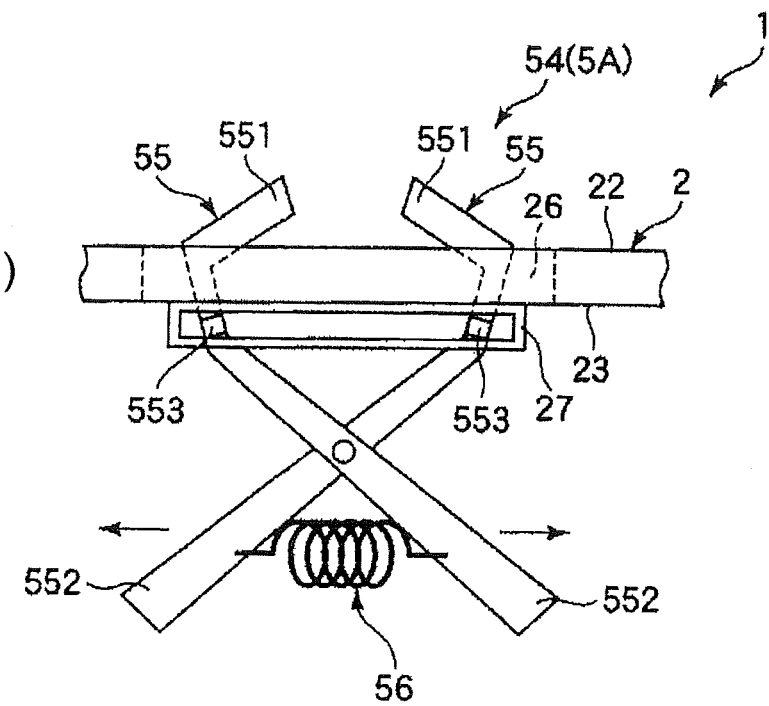
FIGS. 12(a) and 12(b) are views along arrow 12a, 12b in FIG. 11 illustrating a pinching mechanism in its operating state.
Figure 12B:
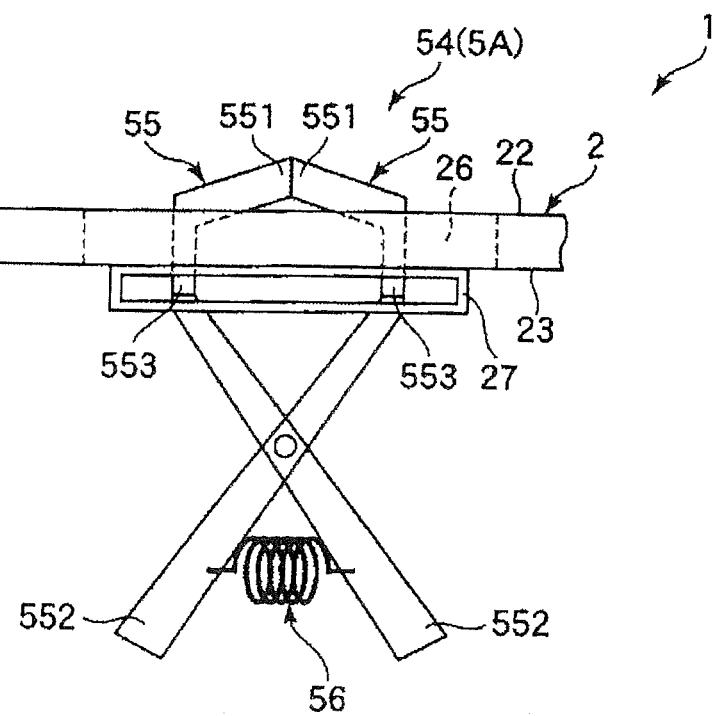

FIGS. 11 and 12 illustrate a third embodiment of an expansion instrument representing another example of the disclosed expansion instrument. The following description focuses primarily on differences between this embodiment of the expansion instrument and the embodiments described above. Features of this third embodiment of the expansion instrument that are the same as features described above are identified by common reference numerals and a detailed description of such features is not repeated.

This third embodiment is the same as the first embodiment above, except for a difference in the configuration of the vaginal-side restriction means.

As shown in FIGS. 11 and 12, in this embodiment, vaginal-side restriction means 5A includes a plurality of (in this embodiment, two) biological tissue holders which, in the illustrated embodiment are constituted by pinching mechanisms (pinchers) 54 each of which has a pair of pinching pieces for pinching (holding or nipping) the biological tissue 300 from the vaginal lumen 200 side. Each of the pinching mechanisms 54 is mounted by being inserted into a mounting portion 26 composed of a through-hole in the vaginal-insertion member 2. The pinching mechanisms 54 are arranged in the vaginal-insertion member 2, at spaced locations along the longitudinal direction (length) of the vaginal-insertion member 2. The pinching mechanisms 54 are the same in configuration; therefore, the pinching mechanism 54 located on the proximal side will be described below on a representative basis. This description applies equally to the other pinching mechanism 54.

As shown in FIG. 12, the pinching mechanism 54 includes a pair of pinching pieces 55 for pinching the biological tissue 300, and a compression coil spring 56 as a biasing member (biasing section) for biasing the pinching pieces 55 en bloc.

The pinching pieces 55 are composed of an elongated body, and nearly central portions in the longitudinal direction of the pinching pieces 55 are rotatably interlocked to each other. In addition, one-side end portions 551 of the pinching pieces 55 that are located on the urethral-insertion member 3 side face each other. This structure helps ensure that the one-side end portions 551 of the pinching pieces 55 can come or move closer together (see FIG. 12(*a*)) and come or move farther apart (see FIG. 12(*b*)), and, when they come closer together, a pinching force for pinching the biological tissue 300 can be obtained. The end portions 551 of the pinching pieces 55 project from the surface of the vaginal-insertion member 2 directly facing the wards the urethral-insertion member 3, and the end portions 551 of the pinching pieces 55 project towards the urethral-insertion member 3.

In addition, the pinching pieces 55 are each provided with a guide pin 553 projecting from the pinching piece. The guide pins 553 can slide along a guide rail 27 provided on the vaginal-insertion member 2. With the guide pins 553 slid along the guide rail 27, in the state where the pinching mechanism 54 is mounted in the mounting portion 26, the pinching pieces 55 can be stably brought closer together or farther apart.

The compression coil spring 56 is disposed between other-side end portions 552, on the side opposite to the one-side end portions 551, of the pinching pieces 55. This helps ensure that in an initial state shown in FIG. 12(*a*), the pinching pieces 55 are biased in the directions of the arrows in the figure, namely, in the directions for releasing the pinching force, resulting in a state where the one-side end portions 551 of the pinching pieces 55 are wide open (apart from each other). When the other-side end portions 552 of the pinching pieces 55 are pressed against the biasing force of the compression coil spring 56, as shown in FIG. 12(*b*), the one-side end portions 551 move closed together, whereby a pinching force can be obtained, in other words, the biological tissue 300 is pinched. For the purpose of maintaining the pinching force obtained by the pressing operation, a lock mechanism similar to that adopted in ordinary surgical forceps is preferably provided at the other-side end portions 552.

In the vaginal-side restriction means 5A configured as above, an operation of the pinching piece 55 in the state where the vaginal-insertion member 2 is inserted in the vaginal lumen 200 permits the biological tissue 300 to be pinched from the vaginal lumen 200 side. As a result, the biological tissue 300 can be drawn toward the vaginal-insertion member 2, and the positional relationship of the vaginal-insertion member 2 with respect to the biological tissue 300 can be restricted or fixed.

Then, with the vaginal-insertion member 2 is brought away from the urethral-insertion member 3 while maintaining this positional relationship, the biological tissue 300 is forcibly pulled in the direction of bringing away or moving away. As a result, the biological tissue 300 becomes the expanded portion 301, so that a surgical treatment (a dissection operation and a puncturing operation) on the expanded portion 301 can be carried out easily and assuredly.

The number of the pinching mechanism(s) 54 arranged is two in this embodiment, but this is not restrictive; for example, the number may be one or more than two.

Figure 13A:
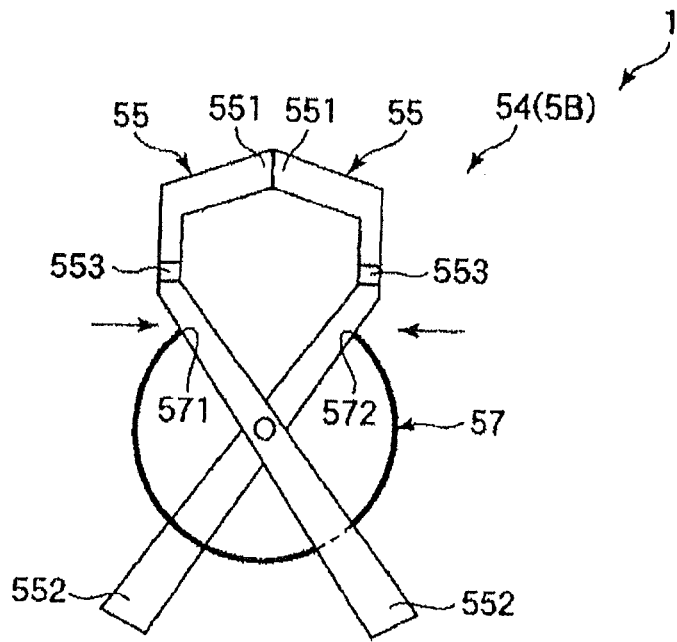
FIGS. 13(a) and 13(b) illustrate operating states of a pinching mechanism in an expansion instrument according to another embodiment disclosed here.
Figure 13B:
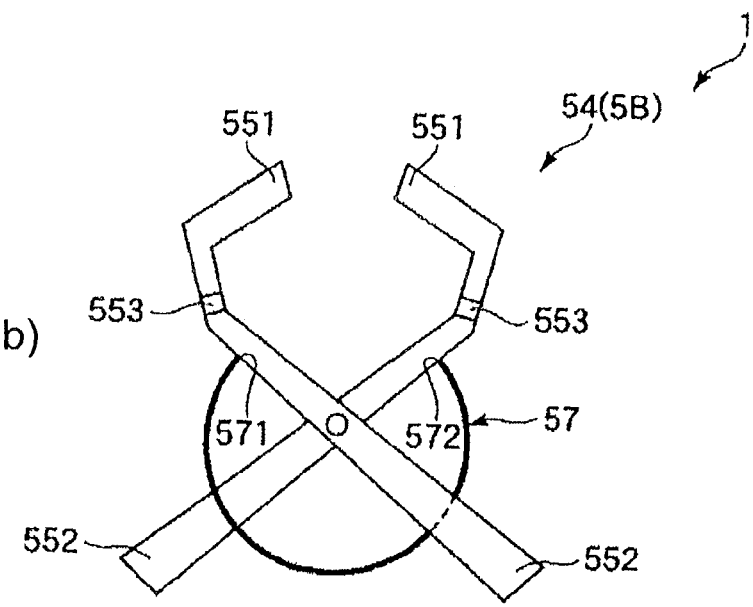

FIGS. 13(*a*) and 13(*b*) illustrate a fourth embodiment of an expansion instrument representing another example of the disclosed expansion instrument, wherein FIGS. 13(*a*) and 13(*b*) illustrate operating states of the pinching mechanism. The following description focuses primarily on differences between this embodiment of the expansion instrument and the embodiments described above. Features of this fourth embodiment of the expansion instrument that are the same as features described above are identified by common reference numerals and a detailed description of such features is not repeated.

This embodiment is the same as the third embodiment, except for a difference in the configuration of the pinching mechanism.

As shown in FIGS. 13(*a*) and 13(*b*), in this embodiment, each pinching mechanism 54 of vaginal-side restriction means 5B has a spring 57 in the shape of letter "C" (ring-like shape), as a biasing member for biasing the pinching pieces 55 in the directions for generating a pinching force. One end 571 of the spring 57 engages one 55 of the two pinching pieces 55, whereas the other end 572 of the spring 57 engages the other 55 of the two pinching pieces 55. This helps ensure that in an initial state shown in FIG. 13(*a*), the pinching pieces 55 are biased in the directions of arrows in the figure, namely, in the directions for generating the pinching force, resulting in a state where the one-side end portions 551 of the pinching pieces 55 are closed together. This configuration makes it possible to pinch the biological tissue 300, draw the biological tissue 300 toward the vaginal-insertion member 2, and thereby restrict the positional relationship of the vaginal-insertion member 2 with the biological tissue 300.

Then, with the vaginal-insertion member 2 brought away or moved away from the urethral-insertion member 3 while maintaining this positional relationship, the biological tissue 300 is forcibly pulled in the direction of bringing away or moving away. Consequently, the biological tissue 300 becomes the expanded portion 301, so that a surgical treatment (a dissection operation and a puncturing operation) on the expanded portion 301 can be carried out rather easily and assuredly.

On the other hand, when the other-side end portions 552 of the pinching pieces 55 are pressed against the biasing force of the spring 57, as shown in FIG. 13(*b*), the one-side end portions 551 are put into an opened state (apart from each other), whereby the pinching force is released.

Figure 14:
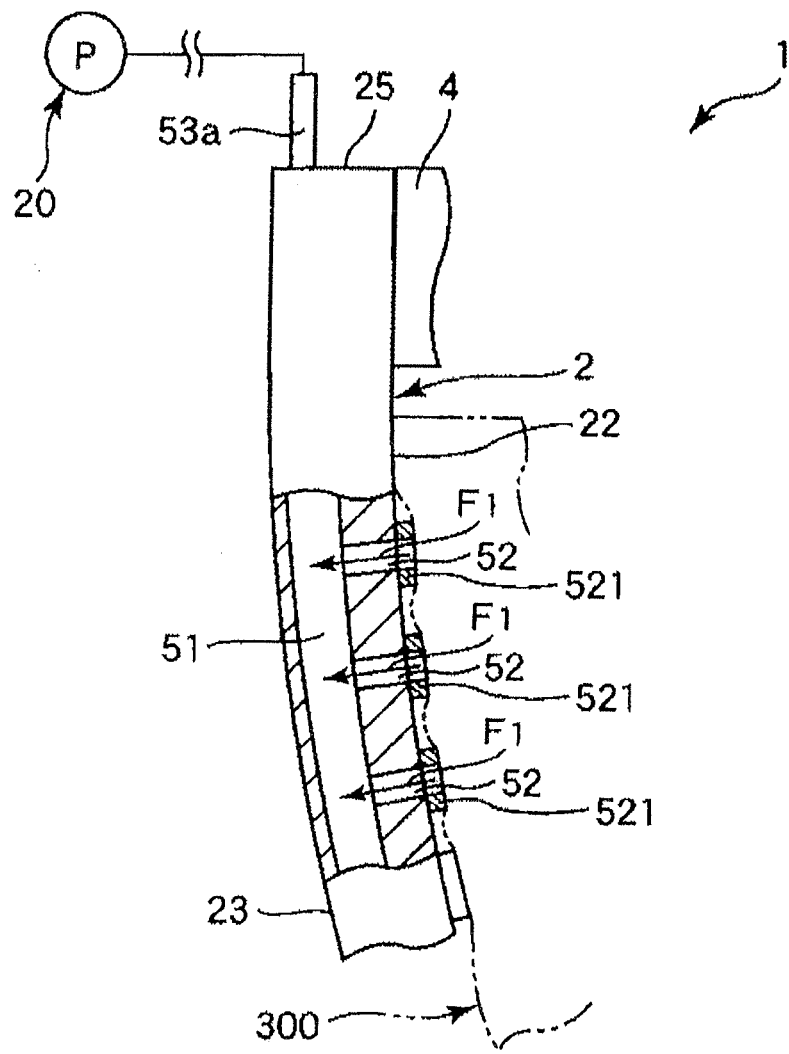
FIG. 14 is a partial longitudinal cross-sectional view of a fifth embodiment of an expansion instrument disclosed here.

FIG. 14 illustrates a fifth embodiment of an expansion instrument representing another example of the disclosed expansion instrument. The following description focuses primarily on differences between this embodiment of the expansion instrument and the embodiments described above. Features of this fifth embodiment of the expansion instrument that are the same as features described above are identified by common reference numerals and a detailed description of such features is not repeated.

This embodiment is the same as the first embodiment above, except for a difference in the configuration of the vaginal-side restriction means.

As shown in FIG. 14, in this embodiment, the suction ports 52 each have a projection 521. The projection 521 projects toward the urethral-insertion member 3 side (the left side in FIG. 4) from the surface 22 on the inside of the curvature of the vaginal-insertion member 2. The projection 521 is ring-like in shape as viewed from the side of the surface 22 on the inside of the curvature.

These projections 521 help ensure that when the vaginal-insertion member 2 is pressed against the biological tissue 300, the projections 521 enhance the adhesion between the vaginal-insertion member 2 and the biological tissue 300 (vaginal wall). As a result, the air-tightness of the inside of the internal space 51 can be secured more stably.

The suction ports 52 respectively have the projections 521 in the illustrated configuration, but this is not restrictive; for example, some of the suction ports 52 may lack the projections 521.

Figure 15:
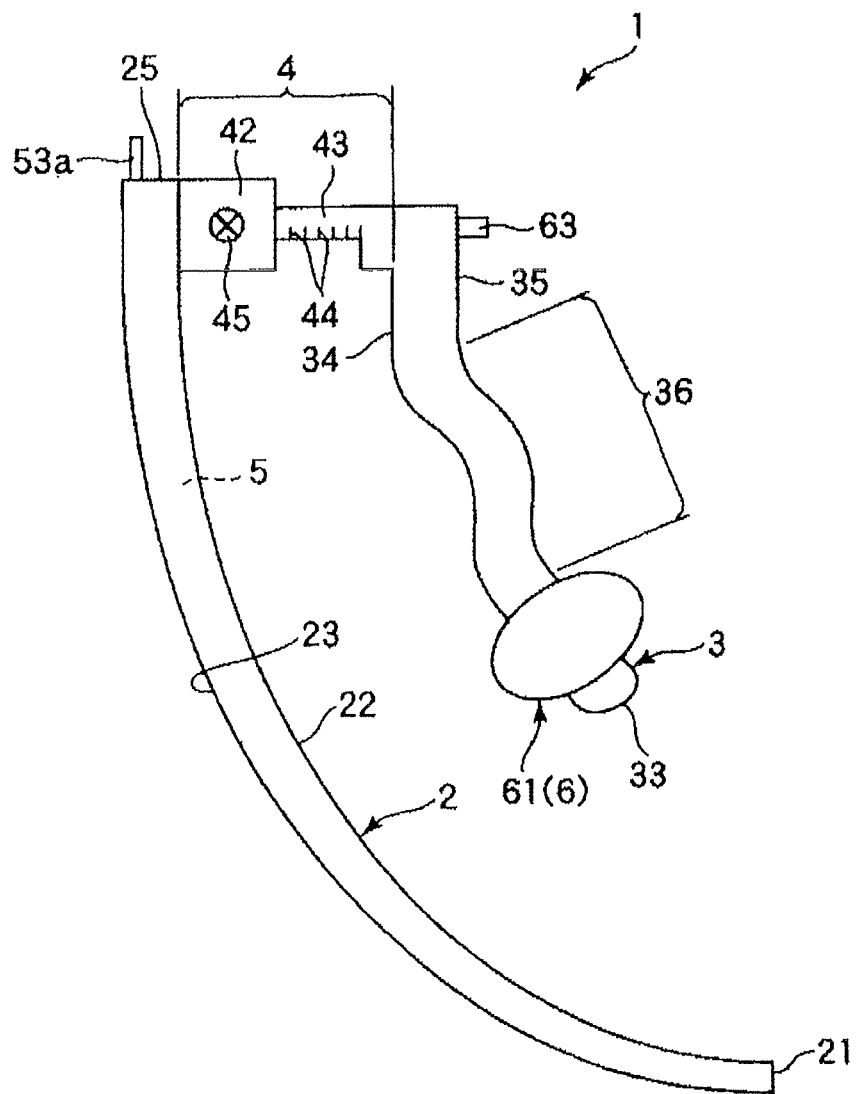
FIG. 15 is a side view of a sixth embodiment of an expansion instrument disclosed here.

FIG. 15 illustrates a sixth embodiment of an expansion instrument representing another example of the disclosed expansion instrument. The following description of the sixth embodiment focuses primarily on differences between this embodiment of the expansion instrument and the embodiments described above. Features of this sixth embodiment of the expansion instrument that are the same as features described above are identified by common reference numerals and a detailed description of such features is not repeated.

This embodiment is the same as the first embodiment above, except for a difference in the shape of the urethral-insertion member.

As shown in FIG. 15, in this embodiment, the urethral-insertion member 3 has a deformation section 36 where a part of the urethral-insertion member 3, specifically an intermediate part in the longitudinal direction of the urethral-insertion member 3, is deformed in a waveform shape in the side view. When the urethral-insertion member 3 is inserted into the urethral lumen 100, a part of the urethral lumen 100 that faces the deformation section 36 can be widened in the direction for bringing the urethral lumen 100 and the vaginal lumen 200 farther apart. As a result, the expanded portion 301 can be formed in the biological tissue 300 more assuredly.

While the expansion instrument disclosed here has been described above referring to the embodiments illustrated in the drawings, the invention is not restricted to the illustrated and described embodiments. Components of the expansion instrument can be replaced by differently configured components that exhibit a similar function, and features and structures may be added.

The expansion instrument disclosed here may be an expansion instrument obtained by combining two or more configurations (features) from amongst the above embodiments.

The expansion instrument disclosed here generally includes an elongated vaginal-insertion member insertable into a vaginal lumen, from among the vaginal lumen and a urethral lumen which are adjacent to each other with biological tissue interposed therebetween; an elongated urethral-insertion member insertable into the urethral lumen; interlock means for interlocking the vaginal-insertion member and the urethral-insertion member so as to allow the insertion members to be brought closer together and brought farther apart; and vaginal-side restriction means for restricting a positional relationship, with respect to the biological tissue, of the vaginal-insertion member having been inserted into the vaginal lumen, wherein the vaginal-side restriction means is provided on the vaginal-insertion member, wherein in a state where the vaginal-insertion member has been inserted into the vaginal lumen, the urethral-insertion member has been inserted into the urethral lumen, and the positional relationship has been restricted by operation of the vaginal-side restriction means, bringing the vaginal-insertion member away from the urethral-insertion member widens the biological tissue in the direction of bringing away.

Therefore, at the time of applying a surgical treatment to the biological tissue between the vaginal lumen and the urethral lumen, the treatment can be carried out rather easily and assuredly.

The detailed description above describes embodiments of an expansion instrument disclosed by way of example. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method comprising:
inserting an elongated vaginal-insertion member into a vaginal lumen positioned adjacent a urethral lumen, with biological tissue located between the vaginal lumen and the urethral lumen;
inserting an elongated urethral-insertion member into the urethral lumen, the vaginal-insertion member and the urethral-insertion member being spaced apart from one another by a distance; and
holding a portion of the biological tissue located between the vaginal lumen and the urethral lumen while increasing the distance between the vaginal-insertion member and the urethral-insertion member to increase a width of the biological tissue located between the vaginal lumen and the urethral lumen.

2. The method according to claim 1, wherein the holding of the portion of the biological tissue located between the vaginal lumen and the urethral lumen includes creating suction inside the vaginal-insertion member to hold the biological tissue in contact with a surface of the vaginal-insertion member.

3. The method according to claim 2, wherein the surface of the vaginal-insertion member contacted by the biological tissue is a curved surface.

4. The method according to claim 2, wherein the vaginal-insertion member includes at least one interior chamber in fluid communication with a plurality of spaced apart suction ports, and wherein the suction is created by operating a pump connected to the chamber.

5. The method according to claim 2, wherein the vaginal-insertion member includes a plurality of interior chambers separated from one another by a wall, each of the interior chambers being in fluid communication with a plurality of spaced apart suction ports, and wherein the suction is created by operating pumps each connected to a respective one of pumps.

6. The method according to claim 1, further comprising, before the holding of the portion of the biological tissue located between the vaginal lumen and the urethral lumen, decreasing the distance between the vaginal-insertion member and the urethral-insertion member to bring a surface of the vaginal-insertion member into contact with the biological tissue.

7. The method according to claim 6, wherein the holding of the portion of the biological tissue located between the vaginal lumen and the urethral lumen includes creating suction inside the vaginal-insertion member to hold the biological tissue in contact with a surface of the vaginal-insertion member.

8. A method comprising:
adjusting a distance between an elongated vaginal-insertion member and an elongated urethral-insertion member so that the elongated urethral-insertion member is spaced apart from the elongated vaginal-insertion member;
inserting the elongated vaginal-insertion member into a vaginal lumen in a vagina of a patient while the elongated urethral-insertion member is spaced apart from the elongated vaginal-insertion member;
inserting the elongated urethral-insertion member into a urethral lumen of a urethra of the patient that is spaced apart from the vaginal lumen, with biological tissue located between the vaginal lumen and the urethral lumen;
fixing a position of the elongated urethral-insertion member in the urethral lumen to prevent the elongated urethral-insertion member from being drawn-out of the urethral lumen;
applying a force that causes the biological tissue between the vaginal lumen and the urethral lumen to contact the elongated vaginal-insertion member; and
increasing the distance between the elongated vaginal-insertion member and the elongated urethral-insertion member while continuing to apply the force that causes the biological tissue between the vaginal lumen and the urethral lumen to contact the elongated vaginal-insertion member to widen the biological tissue located between the vaginal lumen and the urethral lumen so that the biological tissue is expanded biological tissue.

9. The method according to claim 8, wherein the applying of the force that causes the biological tissue to contact the elongated vaginal-insertion member includes applying suction that draws the biological tissue into contact with the elongated vaginal-insertion member.

10. The method according to claim 8, wherein the applying of the force that causes the biological tissue to contact the elongated vaginal-insertion member includes applying the force so that the biological tissue contacts a curved surface of the elongated vaginal-insertion member.

11. The method according to claim 8, wherein the applying of the force that causes the biological tissue to contact the elongated vaginal-insertion member includes creating suction inside the elongated vaginal-insertion member to draw the biological tissue towards and into contact with a surface of the elongated vaginal-insertion member.

12. The method according to claim 11, wherein the elongated vaginal-insertion member includes at least one interior chamber in fluid communication with a plurality of spaced apart suction ports, and wherein the suction is created by operating a pump connected to the chamber.

13. The method according to claim 11, wherein the elongated vaginal-insertion member includes a plurality of interior chambers separated from one another by one or more walls, each of the interior chambers being in fluid communication with a plurality of spaced apart suction ports, and wherein the suction is created by operating pumps each connected to a respective one of pumps.

14. The method according to claim 8, wherein the fixing of the position of the elongated urethral-insertion member in the urethral lumen includes inflating a balloon located at a distal end portion of the elongated urethral-insertion member after inserting the elongated urethral-insertion member into the urethral lumen.

15. The method according to claim 8, further comprising creating a puncture hole in the expanded biological tissue.

* * * * *